(12) United States Patent
Suzuki et al.

(10) Patent No.: US 7,335,191 B2
(45) Date of Patent: Feb. 26, 2008

(54) DISPOSABLE DIAPER HAVING TAPE FOR DISPOSAL THEREOF

(75) Inventors: Seiji Suzuki, Kagawa-ken (JP); Keiichi Jibiki, Kagawa-ken (JP); Nariaki Shimoe, Kagawa-ken (JP)

(73) Assignee: Uni-Charm Corporation, Ehime-Ken (JP)

( * ) Notice: Subject to any disclaimer, the term of this patent is extended or adjusted under 35 U.S.C. 154(b) by 401 days.

(21) Appl. No.: 10/183,811

(22) Filed: Jun. 26, 2002

(65) Prior Publication Data

US 2003/0004486 A1    Jan. 2, 2003

(30) Foreign Application Priority Data

Jun. 29, 2001    (JP)    ............................. 2001-200173
Aug. 23, 2001   (JP)    ............................. 2001-253572

(51) Int. Cl.
*A61F 13/15*    (2006.01)
*A61F 13/20*    (2006.01)

(52) U.S. Cl. ................................. 604/385.13

(58) Field of Classification Search ........... 604/385.01, 604/385.02, 385.13, 389–392; 24/304
See application file for complete search history.

(56) References Cited

U.S. PATENT DOCUMENTS

| | | | | |
|---|---|---|---|---|
| 4,047,528 A * | 9/1977 | Karami | ..................... | 604/390 |
| 4,158,363 A * | 6/1979 | Schaar | ..................... | 604/390 |
| 4,237,890 A * | 12/1980 | Laplanche | ................... | 604/390 |
| 4,643,729 A * | 2/1987 | Laplanche | ................... | 604/389 |
| 5,074,293 A * | 12/1991 | Lott et al. | .................... | 602/57 |
| 5,182,156 A * | 1/1993 | Pape et al. | ................... | 428/130 |
| 5,234,517 A * | 8/1993 | Pape et al. | ................... | 156/192 |
| 5,591,521 A * | 1/1997 | Arakawa et al. | .............. | 428/352 |
| 6,264,644 B1 * | 7/2001 | Igaue et al. | ................. | 604/389 |
| 6,371,949 B1 * | 4/2002 | Soga et al. | .............. | 604/385.13 |
| 6,451,000 B1 * | 9/2002 | Hayase et al. | ......... | 604/385.13 |
| 6,656,171 B1 * | 12/2003 | Matsuda et al. | ............ | 604/390 |
| 6,926,704 B2 * | 8/2005 | Andersson et al. | .... | 604/385.13 |
| 2003/0014030 A1 * | 1/2003 | Andersson et al. | .... | 604/385.13 |

FOREIGN PATENT DOCUMENTS

| | | |
|---|---|---|
| EP | 0 623 330 | 11/1994 |
| EP | 0 826 352 | 3/1998 |
| EP | 0 861 642 | 9/1998 |
| JP | U-58-22908 | 2/1983 |
| JP | Y2-8-10305 | 3/1996 |
| WO | WO 94/09736 | 5/1994 |
| WO | WO 01/13842 | 3/2001 |

* cited by examiner

*Primary Examiner*—Michele Kidwell
(74) *Attorney, Agent, or Firm*—Butzel Long

(57) ABSTRACT

A disposable diaper having a backsheet that defines a garment facing surface and an outer surface provided with an adhesive tape for holding the diaper in a rolled-up state. The adhesive tape includes fastening and reinforcing tapes. The fastening tape is folded back in an inner tape section and an outer tape section. The inner tape section is fixed near its end to the backsheet and spaced from the backsheet near a folded portion that is contiguous to the outer tape section. The outer tape section is coated with an adhesive and temporarily fixed to the inner tape section. The reinforcing tape is folded back in two sections in a direction opposite to that in which the fastening tape is folded back. The reinforcing tape is fixed to the inner tape section near the folded portion and is also to the backsheet.

3 Claims, 5 Drawing Sheets

DISPOSABLE DIAPER HAVING TAPE FOR DISPOSAL THEREOF

BACKGROUND OF THE INVENTION

This invention relates to a disposable diaper for absorption and containment of body wastes.

Japanese Utility Model Application No. 1983-22908A discloses an open-type disposable diaper in which its rear waist region is provided in its transversely middle zone with an adhesive tape attached to an outer surface of a backsheet. The adhesive tape extends rectilinearly in a longitudinal direction of the diaper. The adhesive tape has its inner surface fixed at its lower end to the backsheet and coated at its upper end with adhesive. The diaper folded with bodily discharges can be rolled-up and held by the adhesive tape in this rolled-up state. The above-cited Publication illustrates an embodiment in which the upper end of the adhesive tape extends outwardly beyond the waist zone and another embodiment in which the upper end lies inside the absorbent pad's peripheral edge without extending outwardly beyond this peripheral edge into the waist zone.

Japanese Utility Model Publication No. 1996-10305B discloses a pants-type disposable diaper in which its rear waist region is provided at its transversely middle zone with a tape fastener folded up in its longitudinal direction and attached in this folded-up state to an outer surface of the backsheet so that the longitudinal direction of this tape fastener may be vertically oriented. Being unfolded, a free end portion of the tape fastener serving as a fastening portion extend sufficiently beyond a peripheral edge of the waist-opening to hold the diaper in a rolled-up state without anxiety that the rolled-up diaper might be opened again. The above-cited Publication illustrates an embodiment in which the tape fastener is folded back in a Z-shape, i.e., in three sections and another embodiment in which the tape fastener is folded back in four sections.

In the examples of well known diaper as have been described above, both the adhesive tape and the tape fastener have respective lower ends fixed to the backsheet and respective upper ends in a form of free ends extending upwardly of the diaper from the fixed lower ends. It is not apprehended that these adhesive tape and tape fastener might be peeled off from the backsheet so far as these adhesive tape and tape fastener are linearly pulled in an opposite longitudinal direction thereof from the lower ends toward the upper ends. However, if they are pulled in the counter direction, i.e., from the upper ends toward the lower ends, a peeling force is generated between the adhesive tape or the tape fastener and the backsheet, under which the adhesive tape or the tape fastener may be easily peeled off from the backsheet.

SUMMARY OF THE INVENTION

It is an object of this invention to improve a diaper of prior art as has been described above so that an adhesive tape used to roll up a disposable diaper for its disposal is not easily peeled off from the diaper even if the adhesive tape is pulled upward or downward.

According to this invention, there is provided a disposable diaper having a body facing surface and a garment facing surface comprising an adhesive tape provided on the garment facing surface for holding the diaper in a rolled-up state for disposal.

The adhesive tape comprises a first tape and a second tape attached onto the garment facing surface and aligned on an identical straight line. The first tape is folded back in two sections and overlaid so that opposite ends of the first tape point to one direction of the straight line and the two sections defining a first inner tape section lying on the side of the garment facing and a first outer tape section overlaid on the first inner tape section from outside. A surface of the first inner tape section opposed to the garment facing surface is fixed, in a vicinity of the end of the first inner tape section, to the garment facing surface and spaced, in a vicinity of a fold contiguous to the first outer tape section, from the garment facing surface. The first outer tape section is coated, at least partially on its surface opposed to the first inner tape section, with an adhesive so as to be temporarily fixed to at least one of the first inner tape section and the garment facing surface in such a manner as to be released. The second tape is folded back in two sections and overlaid so that opposite ends of the first tape point to an opposite direction of the straight line and these two sections and overlaid defining a second inner tape section lying on the side of the garment facing surface and a second outer tape section overlaid on the second inner tape section from outside. The second tape section is at least partially interposed, in the vicinity of the fold of the first tape, between the first tape and the garment facing surface. The second inner tape section is fixed to the garment facing surface opposed thereto and the second outer tape section is fixed to the first inner tape section opposed thereto.

In embodiments of this invention, Gurley's stiffness of the first and second tape sections is in a range of 0.1-1 mN/25.4 mm as measured by the method A prescribed in Section 6.20 of Japanese Industrial Standards L 1096, and the first tape is elastically stretchable in its longitudinal direction.

DETAILED DESCRIPTION OF THE PREFERRED EMBODIMENTS

Details of a disposable diaper according to this invention will be more fully understood from the description given hereunder in reference to the accompanying drawings.

Figure 1:
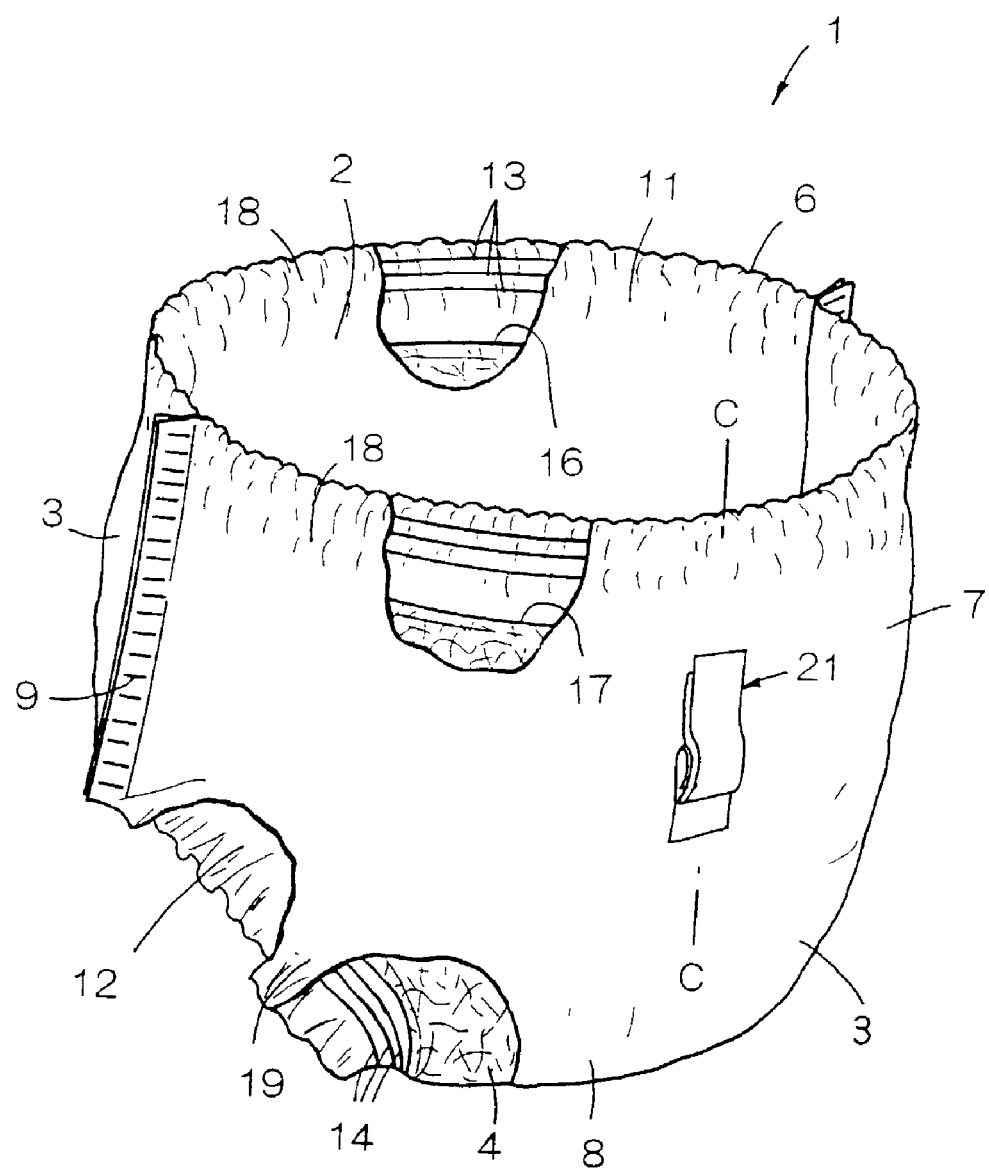
FIG. 1 is a partially cutaway perspective view showing a disposable diaper.

A disposable diaper 1 in FIG. 1 is a pants-type one shown in a partially cutaway perspective view viewed from its backside. The diaper 1 comprises a liquid-pervious topsheet 2 facing a wearer's body of the diaper 1, defining an inner side of the diaper 1, a liquid-impervious backsheet 3 facing the wearer's garment, defining an outer side of the diaper, and a liquid-absorbent core 4 interposed between these two sheets 2, 3. Such diaper 1 is composed of a front waist region 6, a rear waist region 7 and a crotch region 8, covering front, rear and crotch areas of the wearer's torso. The front and rear waist regions 6, 7 have transversely opposite side edge portions, respectively, which are joined together at bonding spots 9 arranged intermittently in a vertical direction along these side edge portions. The core 4 extends upward from the crotch region 8 to its upper ends 16, 17 extend in a waist-surrounding direction in the front and rear waist regions 6, 7, respectively. The diaper 1 has, in addition, a waist-hole 11 and a pair of leg-holes 12. Portions of the top- and backsheets 2, 3 extending outwardly beyond peripheral edges of the core 4 in the vicinity of respective peripheral edges of the waist- and leg-holes 11, 12 are overlaid and bonded together so as to form flaps 18, 19. Waist-surrounding elastic members 13 and thigh-surrounding elastic members 14 are disposed in the flaps 18, 19, respectively, in circumferential directions. These elastic members 13, 14 are secured in a stretched state to the inner surface of at least one of the top- and backsheets 2, 3. In the rear waist region 7 of the diaper 1, an adhesive tape 21 is attached to the outer surface of the backsheet 3 on a center line C-C bisecting a width of the rear waist region 7 in the waist-surrounding direction.

Figure 2:
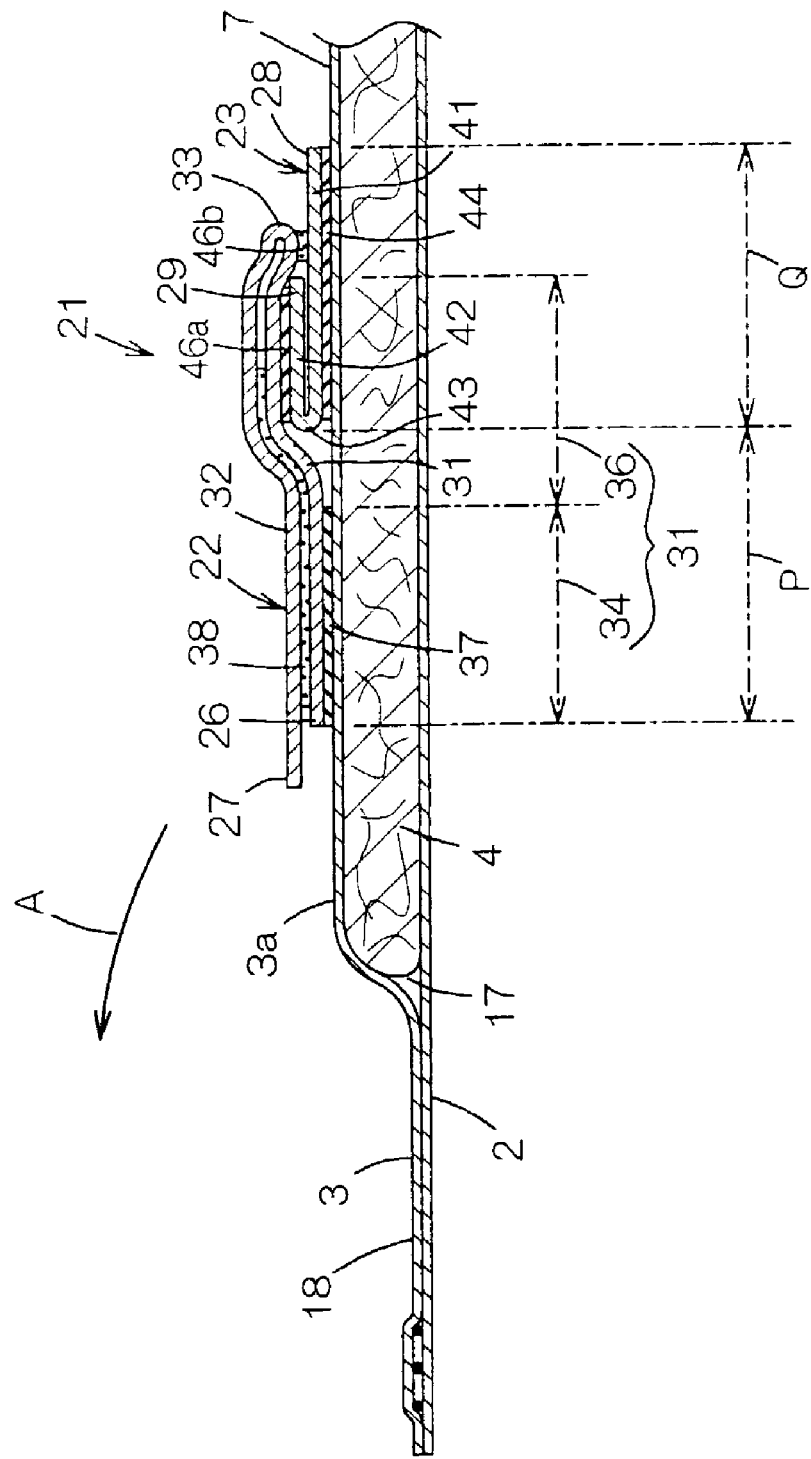
FIG. 2 is a cross-sectional view taken along a line C-C in FIG. 1.
Figure 3:
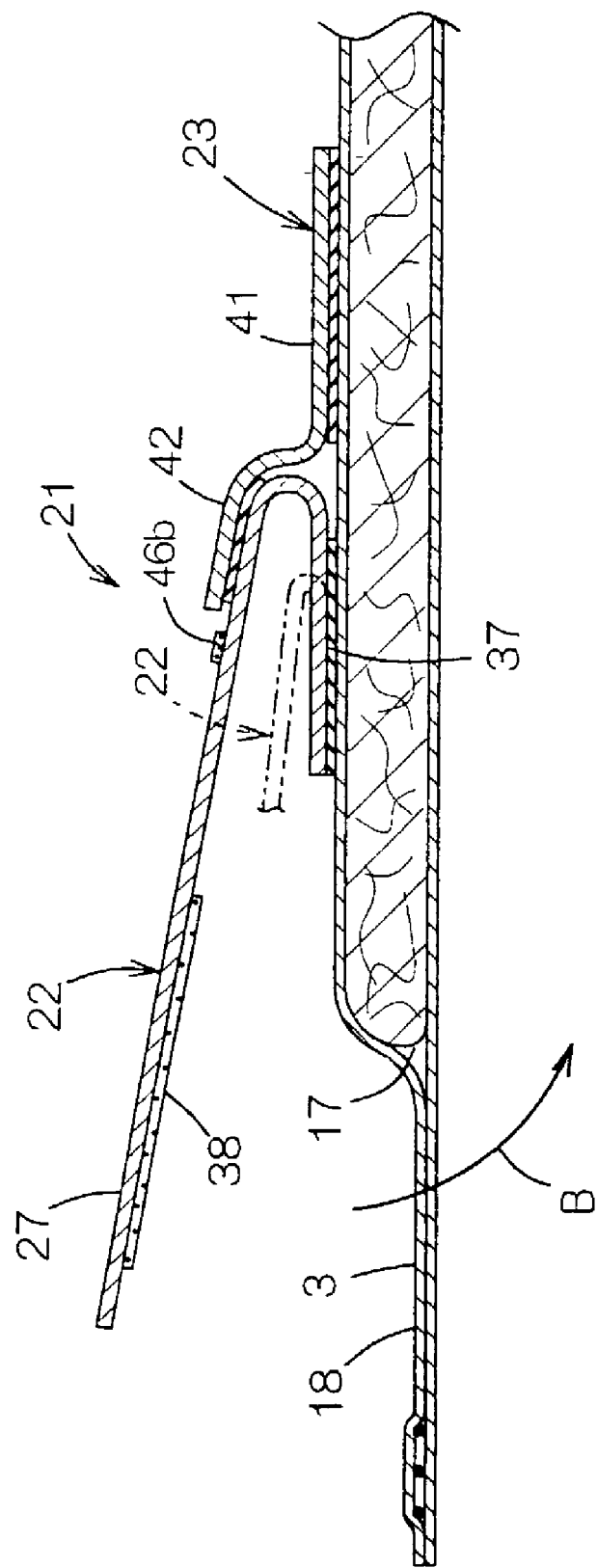
FIG. 3 is a view similar to FIG. 2 but with a tape fastener unfolded.

FIG. 2 is a cross-sectional view taken along a line C-C in FIG. 1, where the upper side of the diaper 1 is shown in the left side of the FIG. 2 and downside of the diaper is shown in the right side of the FIG. 2. The adhesive tape 21 is attached to the backsheet 3 in the rear waist region 7 at a position lower than that of (rightward as viewed in FIG. 2) the upper end 17 of the core 4 (See FIG. 1 also) and in such region where the top- and backsheets 2, 3 and the core 4 overlaid. This adhesive tape 21 really consists of a fastening tape 22 and a reinforcing tape 23 wherein the fastening tape 22 is folded back so that its opposite ends 26, 27 may point to an upward direction (leftward as viewed in FIG. 2) of the diaper 1. The reinforcing tape 23 also is folded back so that its opposite ends 28, 29 may point to a downward direction (rightward as viewed in FIG. 2) of the diaper 1. The end 27 of the fastening tape 22 serves as a finger grip when this tape 22 is unfolded as shown in FIG. 3.

The fastening tape 22 folded back in this manner consists of an inner tape section 31 lying on an outer surface 3a of the backsheet 3 facing the wearer's garment (not shown) and an outer tape section 32 overlaid on the inner tape section 31 from outside wherein these tape sections 31, 32 are contiguous to each other along a fold 33. The inner tape section 31 comprises a fixed portion 34 existing in the vicinity of the end 26 and a deformable portion 36 lying below (rightward as viewed in FIG. 2) the fixed portion 34 and extending to the fold 33 wherein the fixed portion 34 is firmly secured to the backsheet 3 by means of an adhesive 37. The deformable portion 36 is a portion of the fastening tape 22 which turns around together with a second coupling section 42 of the reinforcing tape 23 lying below, as viewed in FIG. 2, as the fastening taper 22 is pulled to a direction indicated by an arrow A with the end 27 held by fingers (see FIG. 3). Except for the vicinity of the end 27 and the fold 33, the outer tape section 32 is coated on its inner surface facing the inner tape section 31 with an adhesive 38. The inner surface of the inner tape section 31 which comes in contact with the adhesive 38 is coated with a release agent (not shown) so that the adhesive 38 may be easily released. The outer tape section 32 is temporarily fixed to the inner tape section 31 in such a manner as to be released.

The reinforcing tape 23 has a first coupling section 41 lying on the outer surface 3a of the backsheet 3 and a second coupling section 42 placed upon the first coupling section 41 from outside wherein these two coupling sections 41, 42 are contiguous to each other along a fold 43. This reinforcing tape 23 is interposed, at least in the vicinity of the fold 43, between the backsheet 3 and the deformable portion 36 of the inner tape section 31 constituting the fastening tape 22. The first coupling section 41 is fixed to the backsheet 3 by means of an adhesive 44 and the second coupling section 42 is fixed to the deformable portion 36 of the inner tape section 31 by means of an adhesive 46a.

In such a state as both the deformable portion 36 of the fastening tape 22 and the second coupling section 42 of the reinforcing tape 23 are fixed as has been described above, the deformable portion 36 may be releasably bonded, in the vicinity of the fold 33, to the first coupling section 41 of the reinforcing tape 23 or the outer surface 3a of the backsheet 3 so as to avoid a possibility that the deformable portion 36 might be peeled off from the backsheet 3 in the vicinity of the fold 33 during use of the diaper 1.

FIG. 3 shows the adhesive tape 21 of FIG. 2 after the outer tape section 32 has been peeled off from the inner tape section 31 by pulling the outer tape section 32 in the direction of the arrow A with the end 27 of the fastening tape 22 held by fingers. With the outer tape section 32 pulled as shown, the second coupling section 42 of the reinforcing tape 23 extending rightward as shown in FIG. 2 swings leftward, i.e., turns around together with the outer tape section 32 and extends in the same direction as that in which the outer tape section 32 extends. The end 27 of the fastening tape 22 shifts from its position in FIG. 2 leftward by a distance corresponding to the length of the second coupling section 42 as the second coupling section 42 turns around. In the case of the diaper 1 as illustrated, the end 27 of the fastening tape 22 shifts from its initial position rightward with respect to the upper end 17 of the core 4 to the position above the flap 18, at which the end 27 of the fastening tape 22 extends upward beyond the upper end 17 of the core 4.

Referring to FIG. 3, the reinforcing tape 23 of which the second coupling section 42 has turned around extends rather rectilinearly in a vertical direction. Even if the fastening tape 22 is further pulled with its end 27 held by fingers, the tensile force is exerted on the fastening tape 22, but does not act on the fixed portion 34. Such behavior of the reinforcing tape 23 is effective to prevent the fastening tape 22 from moving to a position as indicated by imaginary lines and thereby to prevent a peeling force from acting upon the adhesive 37 in the fixed portion 34. In this way, it is unlikely that the fastening tape 22 might be peeled off from the backsheet 3.

Figure 4:
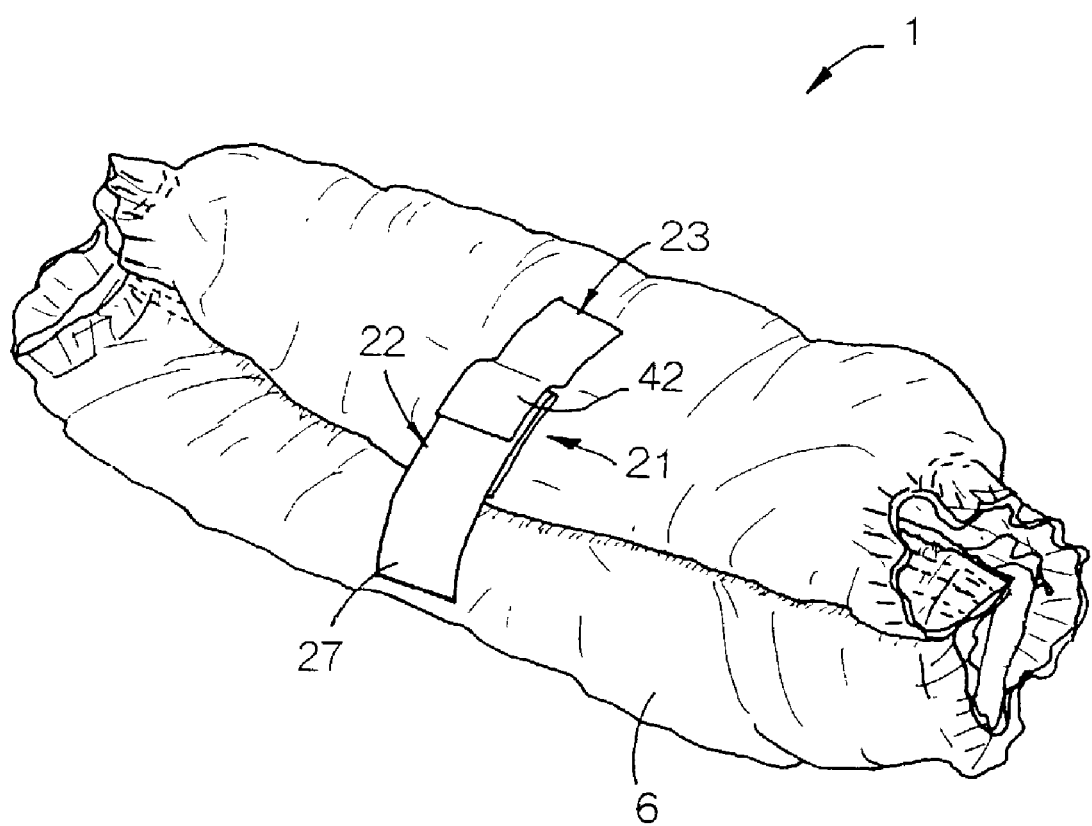
FIG. 4 is a perspective view showing the disposable diaper rolled-up.

FIG. 4 is a perspective view showing the diaper 1 in a rolled-up state using the adhesive tape 21. The diaper 1 having been folded with bodily discharges is rolled-up and held in this state before its disposal in a manner as follows. First, the flap 18 is folded along the upper end 17 in a direction indicated by an arrow B and then the fastening tape 22 having the adhesive 38 is firmly wound around the regions of the diaper 1 such as the crotch region 8 and the front waist region 6 while the diaper 1 is rolled-up. Disposal of the used diaper 1 in this state is preferable from a hygienic point of view. Specifically, even if the used diaper 1 is taken off by tearing along the side edges of the front and rear waist regions 6, 7 joined together at the bonding spots 9, there is no anxiety that the folded regions of the used diaper 1 might be exposed when it is disposed.

The adhesive tape 21 attached to the diaper 1 is appropriately folded during use of the diaper 1 to avoid that the tape 21 might cause any interference and, for disposal of the used diaper 1, the fastening tape 22 is conveniently unfolded so as to be elongated upwardly of the diaper 1 by a dimension corresponding to the length of the second coupling section 42. When the fastening tape 22 is elongated, the reinforcing tape 23 functions to prevent the fastening tape 22 from peeled off from the diaper 1. To assure such preventive effect, the fastening tape 22 and the reinforcing tape 23 are dimensioned so that a relationship of $Q/(P+Q) = 0.1-0.6$, more preferably, $0.2-0.5$ may be established where P represents a dimension of the fastening tape 22 and Q represents a dimension of the reinforcing tape 23. More specifically, the dimension P is a length from the end 26 of the inner tape section 31 constituting the fastening tape 22 to the fold 43 of the reinforcing tape 23 and the dimension Q is a length of the first coupling section 41 constituting the reinforcing tape 23. Plastic film may be used as a material for both the fastening tape 22 and the reinforcing tape 23 of the adhesive tape 21.

It is also possible to form the fastening tape 22 using plastic film which is elastically stretchable in the longitudinal direction of this fastening tape 22. In combination with such fastening tape 22, it is preferred to use the reinforcing tape 23 formed by a plastic film having a stiffness higher than that of the fastening tape 22 and being well resistant to the formation of fine wrinkles. Such a combination is advantageous in that, in the adhesive tape 21 fixed to the backsheet 3 as seen in FIG. 2, the fastening tape 22 temporarily fixed to the reinforcing tape 23 by means of the adhesive 46b might be peeled off from the reinforcing tape 23 in the vicinity of the fold 33. Additionally, it is unlikely that this fold 33 might be peeled off from the back sheet 3 during use of the diaper 1. Therefore the fold 33 will not get stuck on the clothes of the wearer of the diaper.

Figure 5:
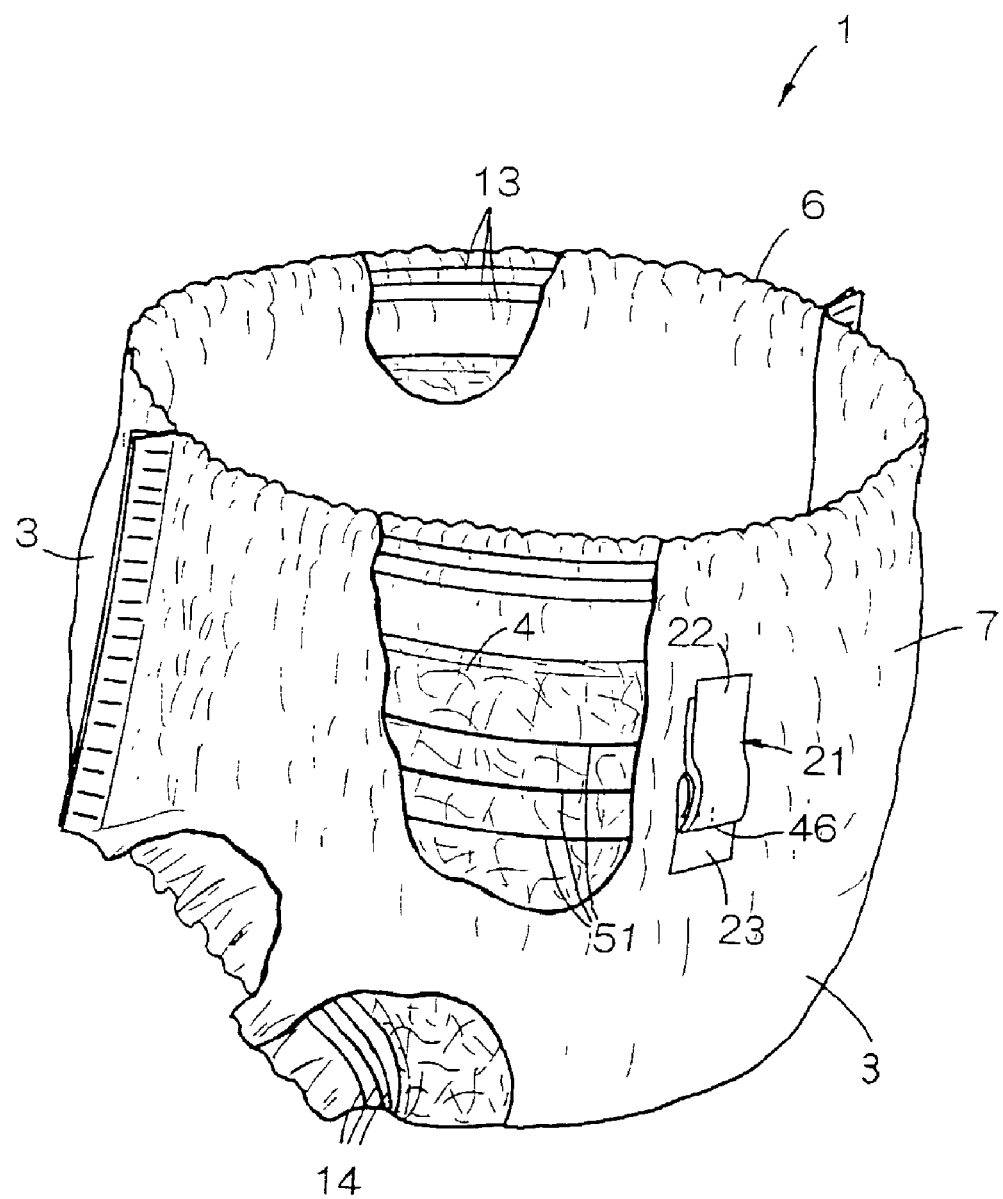
FIG. 5 is a view similar to FIG. 1 showing another preferred embodiment of this invention.

FIG. 5 is a view similar to FIG. 1 showing another preferred embodiment of this invention. In this case, the diaper 1, is provided in at least one of the front and rear waist regions 6, 7 (the rear waist region 7 in this illustrated embodiment) with a plurality of elastic members 51 extending across the core 4 and secured in tension in the waist-surrounding direction thereto. These elastic members 51 are interposed between the backsheet 3 and the core 4 or, if the backsheet 3 comprises two or more sheets, between these sheets and contraction of these elastic members 51 works to bring the core 4 in close contact with the wearer's skin of the diaper. Contraction of these elastic members 51 tends to give a plurality of fine wrinkles on the backsheet 3. However, it is preferred to take some appropriate measures to prevent formation of such fine wrinkles extending to the position of the tape 21 when the adhesive tape 21 is attached to the backsheet 3 in the vicinity of or immediately above the elastic members 51. To achieve the desired effect, this invention uses, as a material for the fastening tape 22 as a well as the reinforcing tape 23, a plastic film having a Gurley's stiffness of 0.1-1 mN/25.4 mm as measured by the method A prescribed by Section 6.20 of Japanese Industrial Standards L 1096. The Gurley's stiffness is measured on the film coated with the adhesive. It should be understood that the adhesive is coated with talcum powder before the film is set on the stiffness tester. The film having a stiffness in a range as has been described above can maintain its surface flat in spite of the presence of the elastic members 51 and there is no anxiety that the fastening tape 22 and the reinforcing tape 23 temporarily bonded to each other by means of the adhesive 46b might be separated from each other during use of the diaper 1. Obviously, such film is free from the formation of the fine wrinkles due to contraction of the waist-surrounding elastic members 13 and the thigh-surrounding elastic members 14.

Without departing from the scope of this invention, the fastening tape 22 as well as the reinforcing tape 23 may be formed by two or more sheets of film having different characteristics, respectively, instead of forming each of the fastening tape 22 and the reinforcing tape 23 using a single sheet of film as is illustrated in the embodiments. While the adhesive tape 21 has been illustrated as a single tape placed on the center line C-C, it is possible without departing from the scope of this invention to provide an appropriate number of the adhesive tape 21 at an appropriate location or locations on the diaper 1 with an appropriate orientation. This invention is applicable also to an open-type diaper.

The disposable diaper according to this invention, the adhesive tape used to roll up the diaper to dispose of comprises the fastening tape and the reinforcing tape. The fastening tape is folded back in two sections and fixed to the outer surface of the diaper only at the end of the inner tape section. The reinforcing tape is folded back in two sections in the direction opposite to the direction in which the fastening tape is folded back. The second coupling section of the reinforcing tape is fixed to the fastening tape in the vicinity of the fold of the inner tape section and the first coupling section of the reinforcing tape is fixed to the outer surface of the diaper. This unique arrangement ensures that the adhesive tape is not peeled off from the diaper even if the outer tape section of the fastening tape is pulled with a considerably strong tensile force in order to use this adhesive tape.

What is claimed is:

1. A disposable diaper having a body facing surface and a garment facing surface, comprising:
    an adhesive tape provided on the garment facing surface for holding the diaper in a rolled-up state for disposal of the diaper;
    said adhesive tape comprising a first tape and a second tape attached to said garment facing surface and aligned along a straight line, said first tape being folded back in two sections so that opposite ends of said first tape point in one direction of said straight line and said two sections defining a first inner tape section lying on a side of said garment facing surface and a first outer tape section overlaid on said first inner tape section from outside, a surface of said first inner tape section opposed to said garment facing surface being fixed, in a vicinity of said end of said first inner tape section, directly to said garment facing surface and spaced, in a vicinity of a fold contiguous to said first outer tape section, from said garment facing surface, and said first outer tape section being coated, at least partially on a surface opposed to said first inner tape section, with an adhesive so as to be temporarily fixed to at least one of said first inner tape section and said garment facing surface in such a manner as to be released; and
    said second tape being folded back in two sections and overlaid so that opposite ends of said second tape point in an opposite direction of said straight line and said two sections defining a second inner tape section lying on the side of said garment facing surface and a second outer tape section overlaid on said second inner tape section from outside, said second tape section being at least partially interposed, in the vicinity of said fold of said first tape, between said first tape and said garment facing surface, said second inner tape section being fixed directly to said garment facing surface opposed thereto and said second outer tape section being fixed to said first inner tape section opposed thereto,
    a dimension P which is a length between the fold of the second tape to a free end of the first inner tape section, and a dimension Q which is a length between the fold of the second tape to a free end of the second inner tape section having the relationship that Q/(P+Q)=0.1-0.6.

2. The diaper according to claim 1, wherein a Gurley's stiffness of said first and second tapes is in a range of 0.1-1 mN/25.4 mm as measured by the method A prescribed in Section 6.20 of Japanese Industrial Standards L 1096.

3. The diaper according to claim 1, wherein said first tape is elastically stretchable in a longitudinal direction.

* * * * *